US006635441B2

(12) United States Patent
Downs et al.

(10) Patent No.: US 6,635,441 B2
(45) Date of Patent: Oct. 21, 2003

(54) MULTI-SAMPLE FERMENTOR AND METHOD OF USING SAME

(75) Inventors: Robert Charles Downs, La Jolla, CA (US); Scott Allan Lesley, San Diego, CA (US); James Kevin Mainquist, San Diego, CA (US); Daniel T. McMullan, San Diego, CA (US); Andrew J. Meyer, San Diego, CA (US); Marc Nasoff, San Diego, CA (US)

(73) Assignee: IRM, LLC, Hamilton (BE)

( * ) Notice: Subject to any disclaimer, the term of this patent is extended or adjusted under 35 U.S.C. 154(b) by 0 days.

(21) Appl. No.: 09/780,591

(22) Filed: Feb. 8, 2001

(65) Prior Publication Data

US 2003/0157591 A1 Aug. 21, 2003

(51) Int. Cl.[7] ............................. C12N 3/00; C12N 5/02; C12N 1/00; C12P 1/00; C12M 1/18
(52) U.S. Cl. ............................. 435/41; 435/27; 435/29; 435/283.1; 435/287.1; 435/288.2; 435/289.1; 435/294; 435/299.1; 435/299.2; 435/300.1; 435/304.1; 435/305.1; 435/305.3; 435/325; 435/808; 435/802; 435/813
(58) Field of Search .............................. 435/21, 29, 41, 435/289.1, 294.1, 299.1, 299.2, 300.1, 304.1, 305.1, 305.3, 283.1, 287.1, 288.2, 325, 802, 808, 813; 935/111

(56) References Cited

U.S. PATENT DOCUMENTS

| | | | |
|---|---|---|---|
| 3,843,809 A | 10/1974 | Luck | |
| 3,997,396 A | 12/1976 | Delente | |
| 4,033,825 A | 7/1977 | Haddad et al. | |
| 4,201,845 A | 5/1980 | Feder et al. | |
| 4,680,266 A | 7/1987 | Tschopp et al. | |
| 4,696,902 A | 9/1987 | Bisconte | |
| 4,774,187 A | 9/1988 | Lehmann | |
| 4,891,310 A | 1/1990 | Shimizu et al. | |
| 4,904,601 A | 2/1990 | Mano et al. | |
| 4,923,817 A | 5/1990 | Mundt | |
| 5,057,428 A | 10/1991 | Mizutani et al. | |
| 5,416,022 A | 5/1995 | Amiot | |
| 5,443,985 A | 8/1995 | Lu et al. | |
| 5,571,720 A | 11/1996 | Grandics et al. | |
| 5,622,819 A | 4/1997 | Herman | |
| 5,686,304 A | 11/1997 | Codner | |
| 5,821,116 A | 10/1998 | Herman | |
| 5,864,395 A | 1/1999 | Laurberg | |
| 5,989,913 A | 11/1999 | Anderson et al. | |
| 6,008,010 A | 12/1999 | Greenberger et al. | |

OTHER PUBLICATIONS

Sigma Cell Culture Catalog, 1994., Sigma Chemical Company, St. Louis, p. 142.*

* cited by examiner

Primary Examiner—Christopher R. Tate
Assistant Examiner—Kailash C. Srivastava
(74) Attorney, Agent, or Firm—Timothy L. Smith; Stacy M. Landry; Quine Intellectual Property Law Group, P.C.

(57) ABSTRACT

A fermentation apparatus is constructed to produce a known and repeatable amount of unpoisoned fermentation product using multiple fermentation vessels. To facilitate further processing compatible with other product processing steps, the fermentation apparatus has an array of sample vessels arranged in a container frame. The container frame is configured to hold the sample vessels during fermentation and to transport the vessel array to or from another processing station. Corresponding to the number of sample vessels in the sample vessel array, a cannula array is configured such that each cannula may be placed inside a sample vessel. The cannula array is attached to a gas distributor that delivers oxygen and/or one or more other gases from a gas source through the cannula into the sample vessel. Because the fermentation volume for each individual sample vessel is smaller than a bulk fermentation apparatus, the fermentation product yields are more predictable and cell growth rates may be more effectively optimized.

27 Claims, 8 Drawing Sheets

MULTI-SAMPLE FERMENTOR AND METHOD OF USING SAME

FIELD OF THE INVENTION

The field of the present invention is fermentation systems. More specifically, the present invention relates to an apparatus and method for simultaneously fermenting multiple samples as part of a multiple process system.

BACKGROUND OF THE INVENTION

Fermentation is a key technology in many fields and industries and is performed both on a mass production scale and on an experimental, bench top scale. For example, fermentation systems are used for the production of a large number of products such as antibiotics, vaccines, synthetic biopolymers, synthetic amino acids, and proteins. Fermentation technology is integral in the production of recombinant proteins using biological organisms such as *E. coli* and many other cell cultures. For example, production of commercial pharmaceuticals such as recombinant insulin (Eli Lilly), erythropoietin (Amgen), and interferon (Roche) all involve fermentation as an essential step.

Fermentation may be conducted on a production scale in order to make commercial quantities of pharmaceuticals or other products. Production scale processes emphasize limited human intervention and automation to increase output and efficiency. In an assembly line fashion, automated equipment enables high throughput processing of production scale amounts of material without disrupting the assembling, testing, or synthesizing process at each individual processing step. For example, automated liquid dispensers, aspirators, and specimen plate handlers facilitate the handling and testing of hundreds of thousands of samples per day, with limited human interaction with the actual sample from start to finish of the entire analysis process. In a further example, sample materials are automatically dispensed into multiple well specimen plates, reagents are added and removed via automated liquid dispensers and aspirators, and the specimen plates are transferred to each successive processing station by automated plate handlers. This increased production efficiency is premised in part on the viability of conducting the entire production process in the specimen plate. Similarly, automated procedures enable the synthesis of commercial pharmaceuticals from starting reagents to finished product without disrupting the production process with cumbersome, inefficient steps such as changing a sample vessel or transferring the sample materials manually to new sample vessels.

Rapid advances in biotechnology have enabled the development of high throughput alternatives to traditional laboratory bench top processes. Unfortunately, fermentation methods have not been amenable to automation because limits in current fermentation technology prevent the uninterrupted processing flow that characterizes automated high throughput systems. Existing fermentation systems typically involve multiple handling steps by either a batch processing method or a continuous processing method.

Current production scale batch processes involve first fermenting in large scale, bulk fermentation vessels, then processing the fermentation medium to isolate the desired fermentation product, followed by transferring this product into the production stream for further processing, and finally cleaning the fermentation apparatus for the next batch. In a large scale batch culture, it is generally necessary to provide a high initial concentration of nutrients in order to sustain cell growth over an extended time. As a result, substrate inhibition may occur in the early stages of cell growth and then may be followed by a nutrient deficiency in the late stages of fermentation. These disadvantages result in suboptimal cell growth rates and fermentation yields. Another disadvantage of this method lies in the need to individually dispense the fermentation products from the bulk fermentation apparatus into separate sample vessels for further processing. Thus, by producing the fermentation product on a bulk scale, the fermentation product is not immediately available for automated processing. Further disadvantages include the decreased efficiency of both transferring the material to another sample vessel, as well as cleaning and sterilizing the fermentation apparatus for the next batch. These disadvantages result in increased production costs, inefficient production times and decreased yields.

Continuous batch processes involve siphoning off the fermentation product from the bulk fermentation vessel and continuously adding nutrients to the fermentation medium according to a calculated exponential growth curve. This curve, however, is merely an approximation that does not accurately predict cell growth in large, industrial scale quantities of fermentation medium. Consequently, due to the unpredictable nature of large scale fermentation environments, experienced personnel are required to monitor the feeding rate very closely. Changes in the fermentation environment may result in either poisoned fermentation products being siphoned off into the production stream or sub-optimal production yields due to starved fermentation mediums. As a further disadvantage, unpredictable fermentation product yields affect the accuracy of subsequent processing steps. For example, when the fermentation yield decreases, the amount of aspirating, the amount of reagent dispensed, or the centrifuge time is no longer optimized, or even predictable. Frequent or continuous monitoring of the fermentation process and adjustment of the fermentation conditions is often not practicable or efficient in a production scale process.

Fermentation remains a key processing step in a number of industries, particularly in biotechnology industries, and thus a need exists for incorporating fermentation processes into current multiple process systems, such as automated high throughput systems. A process that produces a precise, known, and repeatable amount of unpoisoned fermentation product with limited human interaction or sample vessel transfer is essential to integrating fermentation into modem production processes.

SUMMARY OF THE INVENTION

The present invention greatly alleviates the disadvantages of known fermentation systems by providing a fermentation apparatus that may be incorporated into high throughput processing systems.

Briefly, the fermentation apparatus is constructed to produce a known and repeatable amount of unpoisoned fermentation product using multiple fermentation vessels. To facilitate further processing and to be compatible with other product processing steps, the fermentation apparatus preferably has an array of sample vessels arranged in a container frame. The container frame may be configured to hold the sample vessels during fermentation and to transport the vessel array to or from another processing station.

The sample vessels may be arranged in the container frame in an array format to facilitate tracking of the sample vessels during the production process and to make the format of sample vessels compatible with other processing steps. In a preferred embodiment, a total of 96 sample vessels are arranged in an 8×12 format. An arrayed 96-member sample format is compatible with other methods for sample handling such as a 96-well microtiter plate. An 8×12 arrayed format is similarly compatible with sample handling formats designed for greater numbers of sample vessels, such as 384- and 1536-member sample formats, which are multiples of the 96-member sample format.

In a preferred embodiment a cannula array, having a number of cannula corresponding to the number of sample vessels in the sample vessel array, is configured such that each cannula may be placed inside a sample vessel. The cannula array may be attached to a gas distributor that delivers gases from a gas source through the cannula into the sample vessel. Depending on the gas delivered, either aerobic fermentation with agitation or oxygenation or anaerobic fermentation, i.e., with a nitrogen bubbler, for example, can be performed with the present invention. Because the fermentation volume for each individual sample vessel is smaller than a bulk fermentation apparatus, the fermentation product yields are more predictable and cell growth rates are more effectively optimized.

In one aspect the present invention features a method of fermenting a plurality of samples. The method involves the steps of processing a plurality of samples contained in associated sample vessels and fermenting the plurality of samples in the sample vessels. The processing can be done before and/or after the fermenting and the steps preferably are performed at different locations. Each sample preferably is a relatively small, non-bulk volume of material.

An important aspect of the present invention is that a plurality of samples being fermented in associated sample vessels will have similar yields and growth rates. Thus, the plurality of samples may be monitored and harvested at approximately the same, which minimizes the need for human intervention and which produces more predictable fermentation results.

In a preferred embodiment, the method involves the steps of: (a) providing a plurality of sample vessels, each sample vessel having a gripping surface and holding an associated fermentation sample; (b) transporting the plurality of sample vessels to a fermentation apparatus; (c) fermenting each fermentation sample by delivering oxygen, nitrogen or another gas capable of fermenting the sample from a gas source into each sample vessel; (d) manipulating each gripping surface located on each sample vessel; and (e) transferring the sample vessels from the fermentation apparatus to a processing station, wherein processing occurs within the sample vessels. The method may also include the steps of: (1) arranging the sample vessels into an array; (2) arranging a plurality of cannula into a corresponding array such that each cannula may be inserted into an associated corresponding sample vessel; (3) coupling the cannula array to a gas arrangement; and (4) positioning the gas arrangement such that each cannula is inserted into its associated corresponding sample vessel.

In another aspect, the invention provides a multiple process, multiple sample fermentation apparatus. The apparatus includes a means for processesing a plurality of samples contained in associated sample vessels and a means for fermenting the plurality of samples in the sample vessels. The apparatus preferably also includes a process controller.

In a preferred embodiment, the apparatus includes: (a) a fermentation processing station, constructed to receive an array of sample vessels; (b) an array of sample vessels, each sample vessel containing a sample, wherein each sample vessel is capable of undergoing multiple process steps before, during or after fermentation; (c) a gas arrangement positioned to provide oxygen, nitrogen or any other gas capable of fermenting the sample to each sample in the array of sample vessels; (d) a cannula array, configured such that each cannula is attached to the gas arrangement and positionable inside a sample vessel; and (e) a gripping surface on the sample vessel such that a transporter using the gripping surface can transfer the sample vessel from the fermentation processing station to another processing station, wherein the sample is processed directly from the sample vessel. The apparatus may also include: (1) a dispenser, positioned such that feed solution is dispensed within each sample vessel; (2) a sensor with a sample within the sample vessel; and (3) a process controller, configured such that the sensor and the dispenser are in communication with the controller.

Other aspects of the invention feature: (a) methods of moving an array of vessels to a fermentor, and then from a fermentor to a processing station with the assistance of a sample carrier; (b) methods of robotically moving an array of vessels to a fermentor, and then from a fermentor to a processing station; (c) methods of robotically moving a same array of sample vessels from a fermentor to a centrifuge where samples are centrifuged in the same sample vessels; (d) and a fermentor head apparatus.

In preferred embodiments, the fermentations are in sync in the sense that they are roughly growing at the same rate. This allows them to get harvested at the same time. This may be achieved, for example, by use of a negatively regulated promoter. Also, in another preferred embodiment, a certain media plus bubbler increases the amount of soluble protein produced. In yet another preferred embodiment, as noted above, a total of 96 sample vessels are arranged in an 8×12 format or a 384- or 1536-member sample formats is used.

One advantage of the present invention is that the sample vessels are capable of undergoing multiple process steps before, during or after fermentation. Each of these sample vessels has a gripping surface that a transporter uses to transfer the sample vessel to another processing station. These sample vessels are constructed such that post- and pre-fermentation steps may be conducted directly on the sample in the sample vessel. The compatibility of the sample vessel with other processing steps in the production eliminates increased production costs incurred both from first transferring fermentation product from a bulk fermentation vessel to a sample processing vessel, and then cleaning and sterilizing the bulk fermentation vessel. Further, eliminating a transfer step increases the efficiency of the overall process because of the decreased production time in not having to perform an extra transfer step and the increased yield from not losing any fermentation product in a transfer step.

Another advantage is that the fermentation apparatus may also be used in non-production scale environments where uninterrupted process flows are desirable. For example, the fermentation apparatus may be adapted to bench top processes on an experimental scale. This provides a further advantage of easily modifying the process later to an industrial scale by eliminating the step of redesigning the fermentation conditions that is usually required when scaling up a bench top process to a production scale process. Because the present invention utilizes smaller scale fermentation volumes, the unpredictability and unmanageability of bulk fermentation volumes is eliminated while still providing production scale quantities of fermentation product. A fermentation method or apparatus made according to the present invention may be utilized in any production, analysis, or system requiring multiple process steps.

Disadvantages resulting from increased production costs incurred from transferring fermentation product from a bulk fermentation vessel to a processing sample vessel are thus eliminated, as are the costs of cleaning and sterilizing a bulk fermentation apparatus for the next batch. According to the present invention, only the sample vessels will be cleaned at the end of the production process. In addition, valuable time is saved and yields are increased by not having to transfer a bulk fermentation product to a sample vessel that would be amenable to high throughput processing.

A further advantage is that calculation of exponential growth curves is more precise and reliable. This advantage is created because the fermentation volumes of the sample vessels are smaller than current production scale bulk fermentation systems. As a result, the nutrient feed may be more accurately optimized, resulting in the production of known and repeatable yields of fermentation product. In addition, each sample vessel may be equipped with sensors that transmit data to a controller, enabling the apparatus to respond to suboptimal fermentation conditions by appropriately adjusting environmental parameters. The present invention uses relatively small volumes by fermenting in a sample vessel and thereby eliminates the erratic fluctuations in environmental conditions that lead to unpredictability of fermentation growth yields. As a result, for example, the amount of aspirating, the amount of reagent dispensed, or the centrifuge time may now be predicted and optimized, leading to a more efficient and reliable system. The steps of monitoring of the fermentation process to determine the fermentation yield and monitoring or adjusting further processes downstream, such as dispensing or aspirating steps based on the amount of fermentation product, are eliminated when using smaller volume fermentation batches.

Another added advantage stems from the size of the fermentation batches. Because these fermentation batches are relatively small compared to the bulk fermentation vessels currently being used, known amounts of nutrients may be calculated to optimize the fermentation yield and known fermentation yields may be calculated on a predictable and repeatable basis. This reliability in calculating a fermentation yield enables the optimization of centrifuge times, dispensing accurate amounts of reagent, and aspirating accurate amounts of liquid that is otherwise not possible in current bulk fermentation systems. Without a reliable and repeatable fermentation product yield, it is very difficult to engineer a high throughput system involving many processing steps where each processing step, such as the amount dispensed or the time centrifuged, would otherwise vary according to a fluctuating fermentation yield. The present invention overcomes these difficulties by providing predictable and repeatable fermentation yields upon which to calculate and optimize subsequent processing steps, such as those used in a high throughput system.

These and other features and advantages of the present invention will be appreciated from review of the following detailed description of the invention, along with the accompanying figures in which like reference numerals refer to like parts throughout.

DETAILED DESCRIPTION OF THE INVENTION

A multiple-sample fermentor of the present invention, an automated fermentation apparatus of the present invention and a method of using each are described in non-limiting detail below.

I. Multiple-Sample Fermentor

Figure 1:
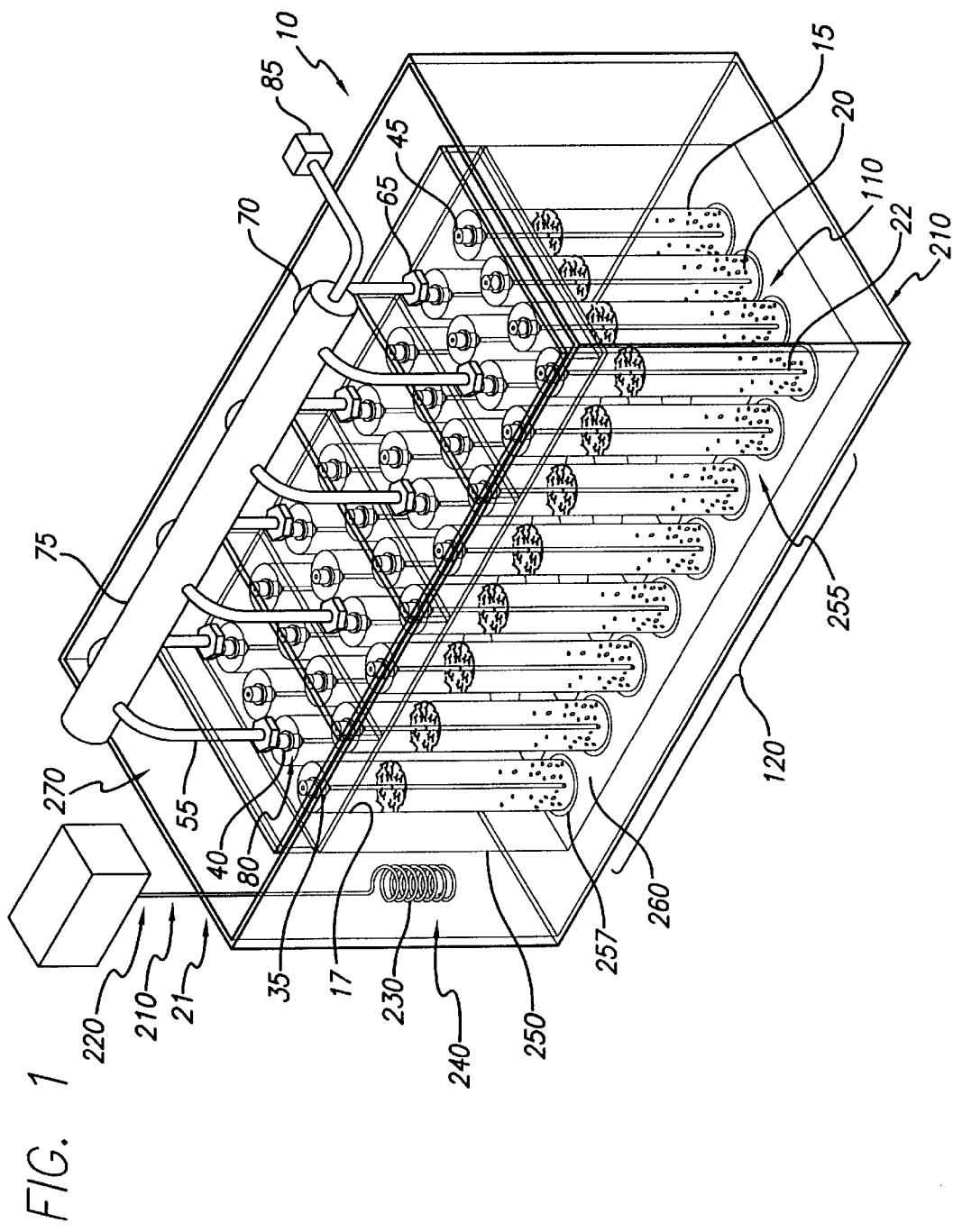
FIG. 1 is a perspective view of a fermentation apparatus in accordance with the present invention.

In accordance with the present invention, a fermentation apparatus 10 is provided in FIG. 1. Fermentation apparatus 10 generally comprises sample holder arrangement 255, cannula assembly 80 and gas distribution arrangement 270. More particularly, the illustrated fermentation apparatus 10 is configured to separately and simultaneously ferment multiple batch samples in sample vessels that are compatible with direct pre- and post-fermentation processing.

Sample holder arrangement 255 is comprised of gripping surfaces 17, individual sample vessels 15, an array of sample vessels 110, a transportable container frame 250, and an array of placement wells 260 corresponding to the array of sample vessels 110. Gripping surfaces 17 are located on each individual sample vessel 15, which collectively form sample vessel array 110. It is preferable that gripping surface 17 resides on the bottom of each sample vessel, but gripping surface 17 can be located on any surface of the sample vessel that enables sample vessel 15 to be transferred to or from another processing station or container frame 250.

In an embodiment shown in FIG. 1, individual sample vessels 15 are configured in a rectangular array 110, but the array may be configured in any physical construct that is conducive to fermentation or that is compatible with other processing steps. For example, a honeycomb, circular, triangular, or linear configuration may be more efficient in other contemplated applications of the present invention. The bottom of each individual sample well 15 is positioned within each placement well 257. The array of placement wells 260 preferably mirrors the configuration of the array of sample vessels 110 and is embedded in transportable container frame 250. Placement wells may, however, be arranged in alternative configurations. For example, placement wells may be arranged as linear troughs, each holding a row of sample vessels. In another embodiment, placement wells are absent from transportable container frame 250.

By using transportable container frame 250, the entire array of sample vessels 110 may be transported to and from one fermentation processing station to another processing station in a multiple process production. In this illustrated example, transportable container frame 250 transports array of sample vessels 110 into a temperature controlled area 210 such as a water bath. In this embodiment, temperature controlled area 210 is comprised of water bath 240 in water bath container 215, which is controlled by water bath temperature controller 220 and temperature coil 230 immersed in water bath 240. Other forms of temperature control may be used, such as temperature controlled gel baths, ovens, glove boxes, or air chambers.

In one embodiment, colonization of bacteria and other preparative steps are performed within sample holder arrangement 255. For example, bacteria and initial nutrients are dispensed into each sample vessel 15 at a prior processing station. Being able to prepare bacteria directly in each individual sample vessel eliminates the need to inoculate a culture and initiate colonization in a separate container before transferring the sample to the fermentation apparatus. Using the sample holder arrangement of the present invention to colonize the fermenting bacteria decreases costs by eliminating a separate colonization arrangement.

The present invention preferably uses fermentation conditions which lead to high level production of soluble proteins. These fermentation conditions may employ the use of high levels of yeast extract and bactotryptone (rich media, referred to as terrific broth or TB). Secondly, this media may be supplemented with 1% glycerol (additional carbon source). Lastly, the media preferably is buffered with high amounts of phosphate (100 mm final concentration, at pH 7.6). The first two additions allow the cells to be grown for up to 10 hours without the apparent loss of nutrients. The highly buffered media prevents the cells from being exposed to high levels of acid (low pH) which routinely occurs during fermentation. In the present invention these liquids preferably are delivered to the cultures up front.

Surprisingly less than 5% of human proteins expressed in normal Luria Broth or LB media, were found to be soluble. Using the above media, 15–20% of human proteins expressed in *E. coli* now appear to be soluble.

In a preferred embodiment, the fermentation media is prepared as follows. TB media is prepared in 7 L batches. Antibiotics are not added to TB media until the day it will be used for a fermentation run. To prepare the 7 L bath, the following steps are performed: (1) Fill a clean 10 L pyrex bottle with ~4 L DI $H_2O$, add a large stirbar; (2) Add 168 g Yeast Extract; (3) Add 84 g Tryptone; (4) Add 70 ml Glycerol; (5) Stir on stirplate until completely dissolved; (6) QS to 6.3 L; (7) Autoclave on the longest liquid cycle. Remove TB media from the autoclave as soon as possible to allow for a quick cool down; (8) Store TB media at room temperature; and (9) Record process. Fermentor Media (TB Media) is the same for all Fermentor runs. The difference in media is the antibiotic(s) added just before fermentation. On the same day of a fermentation run, the following may be added to TB media: (1) 700 ml 1 M KPO4 (pH 7.6); (2) 7 ml Antifoam; (3) 7 ml 20 mg/ml Chloramphenicol; (4) 7 ml 100 mg/ml Ampicillin; (5) Add enough 18MΩH2O to bring the volume up to 7 L; (6) Write everything added to TB media on its label; (7) Cap tightly and shake bottle well; and (8) Record process.

Once the bacteria are colonized, sample holder arrangement 255 is conveniently transported to water bath 240, or any other temperature controlled area 210.

Figure 3:
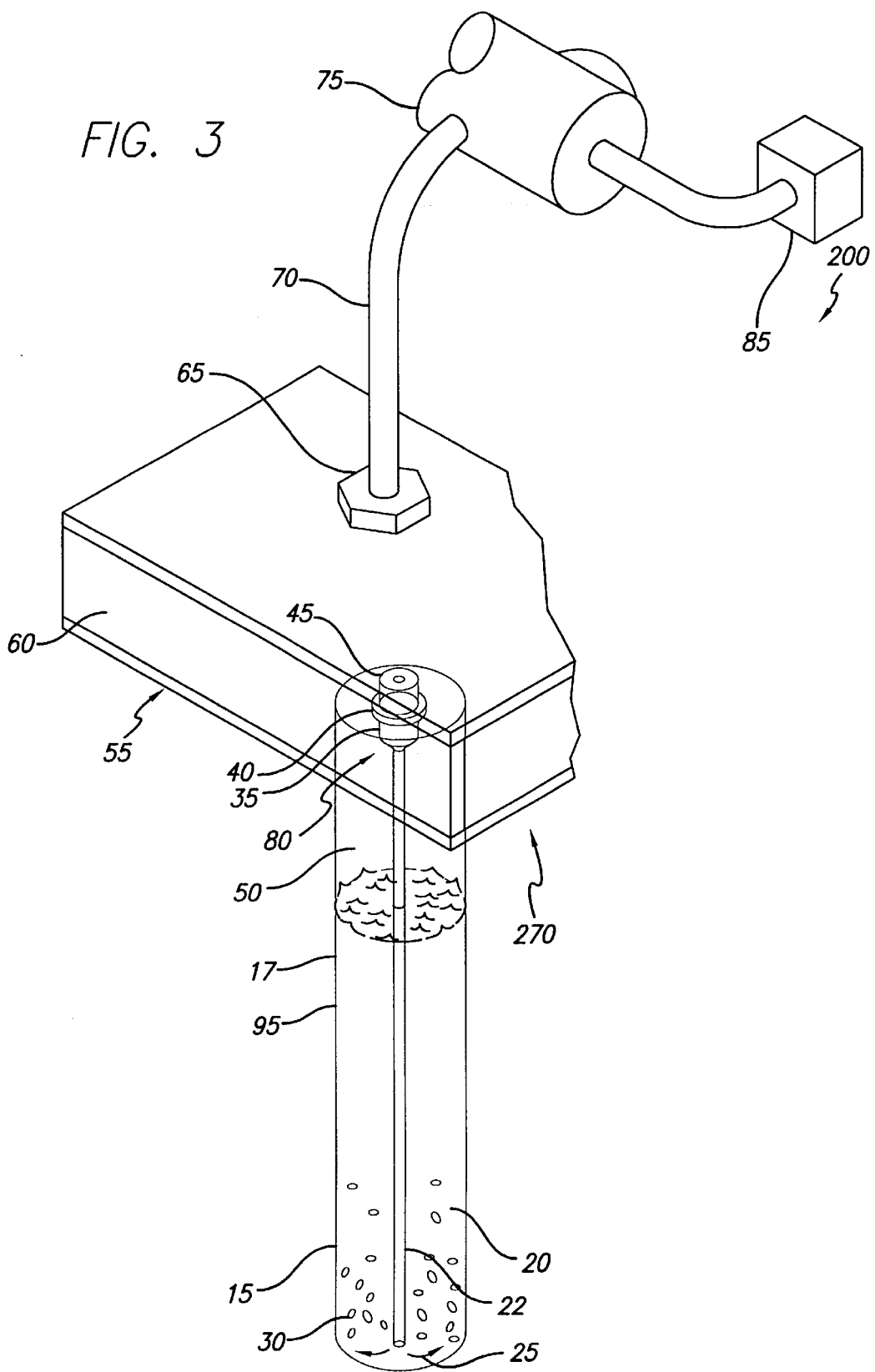
FIG. 3 is a perspective view of an individual fermentation sample vessel in accordance with the present invention.

In the embodiment illustrated in FIGS. 1 and 3, cannula assembly 80 is comprised of an array of cannula 120 composed of individual cannulas 22 that correspond to array of sample vessels 110. Each individual cannula 22 is connected by a fastener 35, which couples cannula 22 to a gas distribution arrangement 270. The cannula 22 preferably extends substantially to the bottom of the individual sample vessel 15 in order to increase aeration and mixing.

In another embodiment, each individual cannula is attached directly to a gas distribution arrangement 270 in an airtight, liquid-tight manner. Eliminating the need for a fastener, this embodiment directly integrates cannula 22 into a gas distribution arrangement 270, thereby decreasing the number of surfaces, grooves and pockets available for possible bacterial contamination, and thus decreasing the opportunities for fermentation spoilage. Likewise, cannula 22 integrated into a gas distribution arrangement 270 may be autoclaved with a gas distribution arrangement 270, thereby eliminating the need to unfasten each cannula 22 separately before cleaning and sterilization. This convenience saves both time and money as well as adding to the uniformity of each batch. For example, the possibility for human error is minimized, because each cannula 22 does not have to be fastened individually before each fermentation run or unfastened individually prior to cleaning and sterilization. Also any non-uniformities in any one cannula 22 will be immediately apparent as an individual cannula 22 will be constantly associated with the same sample vessel in each run.

Figure 8:
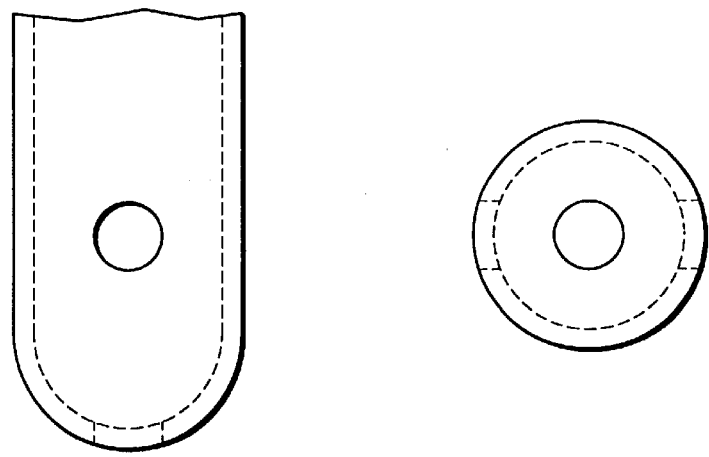
FIG. 8 is cross sectional view of a cannula in accordance with the present invention.

In a preferred embodiment illustrated in FIG. 8, gas flow through cannula 22 is regulated through three passages. Gas flow through passages may be individually or collectively regulated. Smaller gas bubbles are obtained with passages than with a single, larger passage through cannula 22. As a result, gas bubbles formed from these multiple passages have more surface area than bubbles formed from a single passage. In a preferred embodiment, passages are precision drilled in order to more accurately adjust gas flow within each passage and to ensure uniform gas delivery across the set of sample vessels. Fewer or more passages may be used according to the specific application of the present invention. Passages may be the same or different sizes and may be circular or any non-circular shape, such as rectangular, oval, or triangular.

Figure 2:
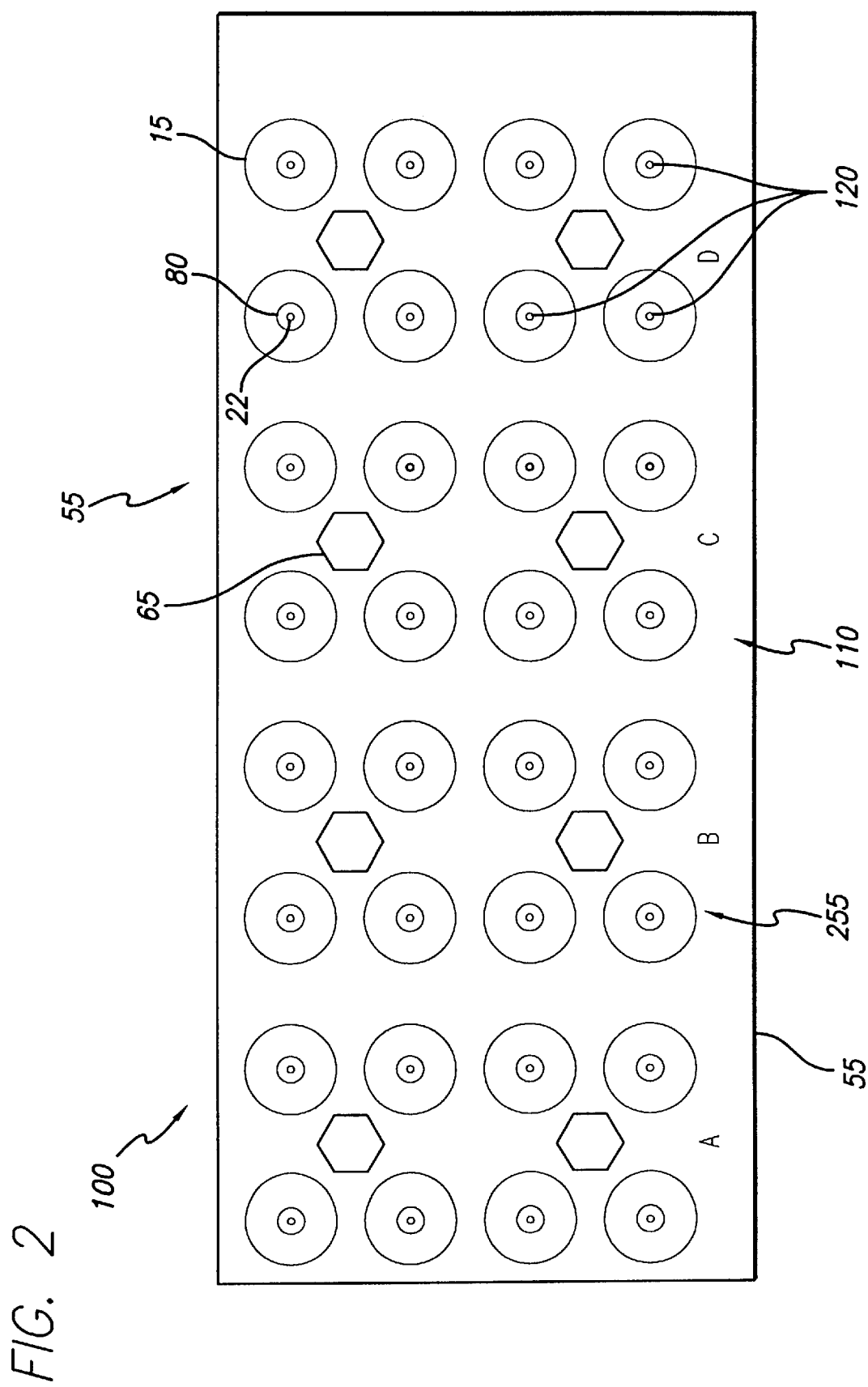
FIG. 2 is a top view of a fermentation apparatus in accordance with the present invention.

In FIGS. 1–3, gas distribution arrangement 270 is comprised of a gas source 85 connected to a manifold 75. Conduit 70 connects manifold 75 to a connector 65. Connector 65 connects manifold 75 to a gas distributor 55.

Gas source 85 preferably is composed of two or more different gases, for example, air and oxygen. Alternatively, different gas sources may be delivered through gas source 85. For example, in one embodiment gas source 85 contains an inlet for $N_2$ gas and an inlet for $O_2$ gas. The ratio of each gas may be controlled either manually or remotely by using a process controller (not shown). The ability to adjust gas ratios enables the present invention to optimize the amount of gas (e.g., oxygen) needed as the growing conditions change throughout the fermentation. Any type, mixture or number of may be introduced and mixed through gas source 85 and provided to a fermentation sample 20 contained in sample vessel 15.

Referring to FIG. 3, gas (e.g., oxygen) is delivered from manifold 75 to all parts of distributor 55 through a hollow space 60 of distributor 55, thus oxygenating, if desired, the entire array of sample vessels 110. Oxygen and/or one or more other gases is delivered from distributor 55 through individual cannula 22, which is connected to distributor 55 by way of cannula assembly 80.

Figure 6:
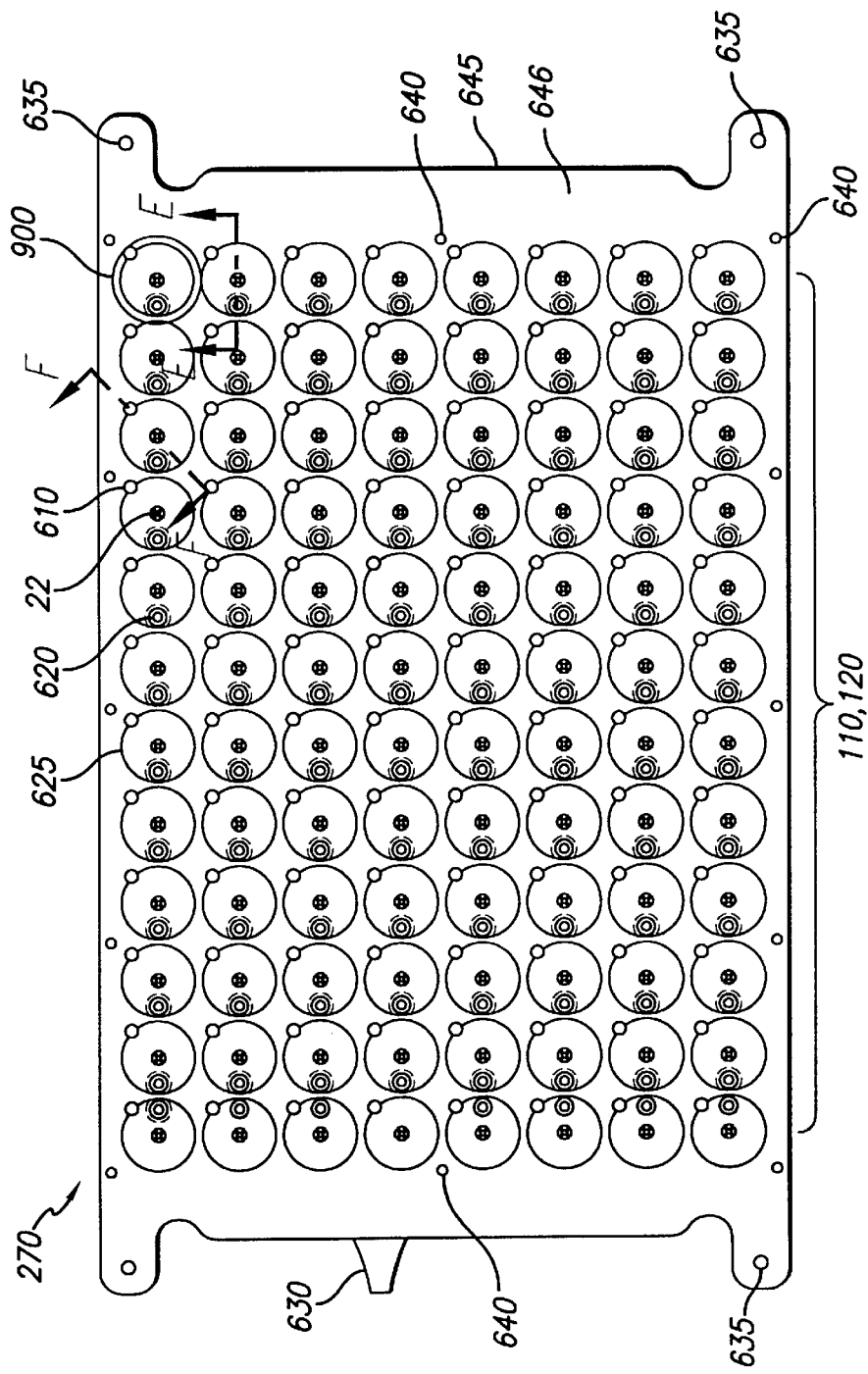
FIG. 6 is a bottom view of a gas arrangement in accordance with the present invention.
Figure 12:
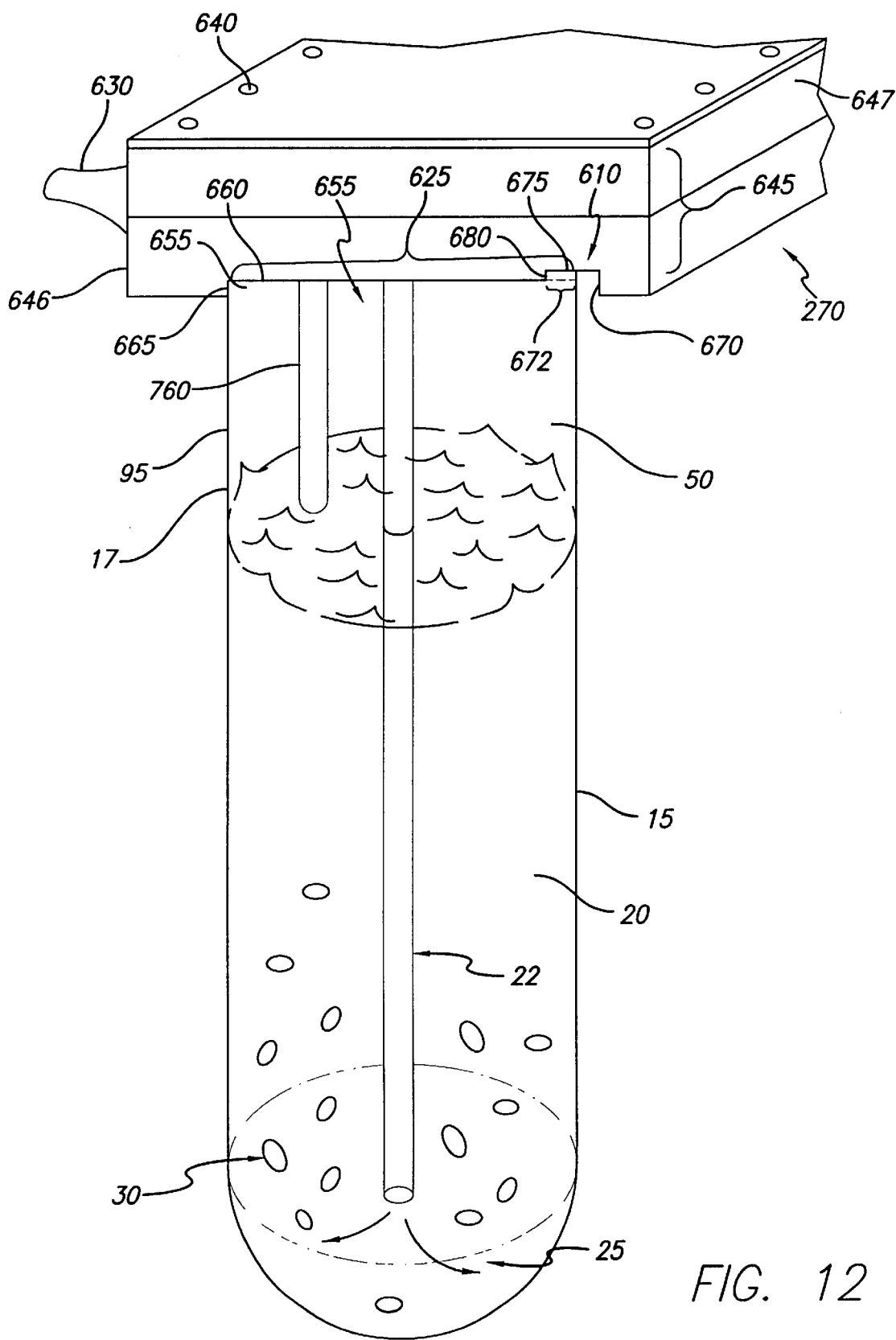
FIG. 12 is a perspective view of an fermentation sample vessel employing a dispensing plate in accordance with the present invention.

In one embodiment, cannula assembly 80 is comprised of a connector 45 on an inside face of distributor 55 as well as connector 40 on an outside face of distributor 55. Fastener 35 attaches individual cannula 22 to connector 40 on distributor 55. Arrows 25 depict oxygen and/or one or more other gases flowing from cannula 22 into fermentation medium 20 and producing gas bubbles 30. For example, gas source 85 may be coupled directly to a dispensing plate 645 without the use of manifold 75, as illustrated in FIGS. 6 and 12. Likewise, cannula assembly 80 may be constructed by alternative methods. For example, as shown in FIG. 12, cannula 22 is attached directly to dispensing plate 645.

In this manner, the exact mixture of gases delivered from gas source 85 is uniformly distributed to each individual cannula assembly 80. Any gas distribution arrangement 270 may be employed that uniformly delivers oxygen, an oxygen containing mixture, or another gas or gas mixture capable of fermenting the sample, from gas source 85 into sample vessel 15.

FIGS. 6 and 12 illustrate a preferred gas distribution arrangement 270 comprised of a dispensing plate 645 directly attached to an array of cannula 120 and that is configured without manifold 75, conduit 70 or manifold connector 65. In this preferred embodiment, dispensing plate 645 is comprised of a bottom portion 646 and a top portion 647 (not shown). Inlet 630 delivers oxygen, an oxygen containing gas mixture, or another gas or gas mixture capable of fermenting the sample, to dispensing plate 645 from gas sources 85 (not shown).

Bottom portion 646 and top portion 647 are aligned and fastened together through apertures 640 to form an air-tight, liquid-tight seal. A hollow space exists between portions 646 and 645 through which gases are uniformly distributed to cannula array 120. Apertures 635 are used to fasten vertical supports to dispensing plate 645 that allow dispensing plate 645 to rest adjacent to array of sample vessels 110. Any suitable fastener may be used. For example, guide pins, rivets, nails, nut/bolt combinations, or magnets may be used. A releasable fastener, such as a screw or nut/bolt combination, is used in a preferred embodiment, although permanent type fasteners, such as adhesives, may be desired in some applications. In the illustrated example, screws connect upper portion 647 and bottom portion 646 to form dispensing plate 645. Screws also fasten aluminum legs to dispensing plate 645 as vertical supports.

Dispensing plate 645 may be composed of any suitable material that maintains the structural integrity of plate 645 during fermentation. For example, dispensing plate 645 may be composed of metal, plastic, ceramic, or any suitable composite. In the illustrated example, dispensing plate 645 is composed of Teflon™-coated aluminum, thus enabling dispensing plate 645 to undergo autoclave sterilization procedures.

Figure 9:
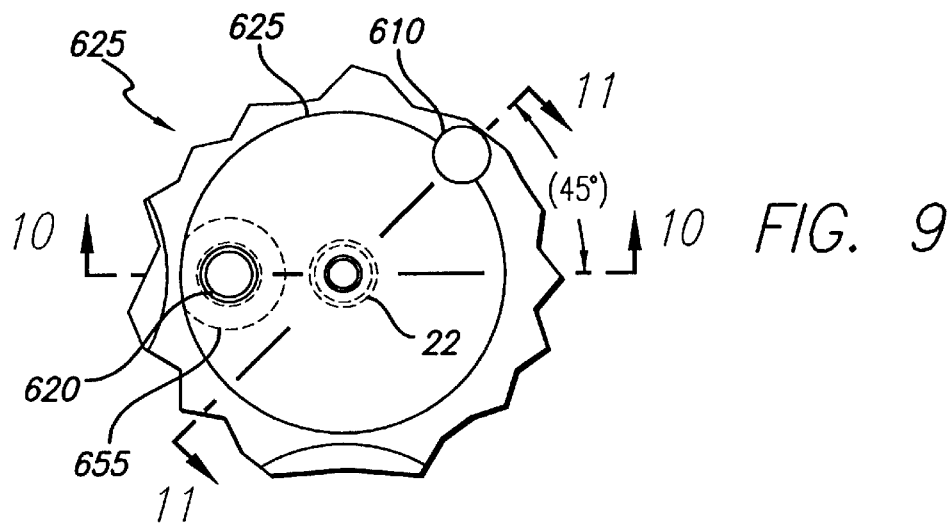
FIG. 9 is a bottom view of a sample vessel area of a dispensing plate shown in FIG. 6 in accordance with the present invention.
Figure 10:
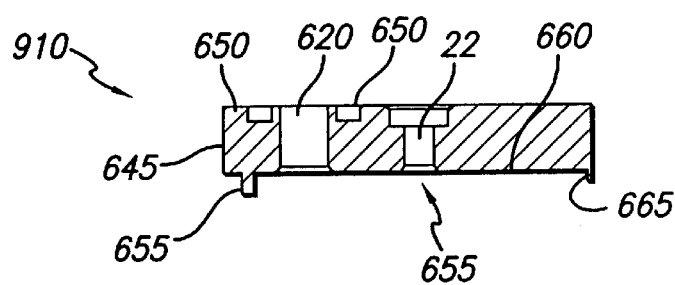
FIG. 10 is a cross sectional view of the sample vessel area shown in FIG. 9 taken along the line E—E in accordance with the present invention.
Figure 11:
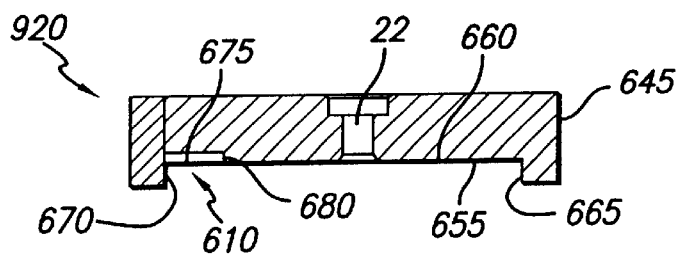
FIG. 11 is a cross sectional view of the sample vessel area shown in FIG. 9 taken along line F—F in accordance with the present invention.

In this embodiment, sample vessel areas 625, preferably located in bottom portion 646, correspond to array of sample vessels 110. FIGS. 9–11 illustrate features encompassed by sample vessel area 625 on bottom portion 646. In this preferred embodiment, cannula 22 is directly attached to bottom portion 646. Aperture 620 holds a dispensing tube 760 (not shown) for dispensing nutrients and other solutions into sample vessel 15. Aperture 620 can be used to access samples during the fermentation process. Pipettes or syringes can be used to draw samples or add nutrients, water, etc. Fastening groove 650 enables dispensing tube 760 to be fastened to dispensing plate 645. Indentation 655 and vertical edge 665 create a circular recess that helps immobilize sample vessel 15 within sample vessel area 625. Although in this embodiment, indentation 655 is circular and corresponds to the shape of sample vessel 655, other suitable shapes may be used.

Vent 610 is positioned on the circumference of sample vessel area 625 and allows gases and built up pressure to escape sample vessel 15. Referring to FIG. 11, vent 610 creates venting space 675. Because vertical edge 670 is larger than vertical edge 665, venting space 675 occupies a deeper recess than recess 655. The difference in height between vertical edges 670 and 665 is equal to the height of vertical edge 680 and determines the depth of venting space 675. Other configurations of venting space 675 and recess 655 (and, accordingly, vertical edges 665, 670, and 680) may be constructed such that built-up pressure within sample vessel 15 can escape through venting space 675 without contaminating other sample vessels.

When the top surface of sample vessel 15 abuts surface 660, gases, liquids, emulsions, or excess pressure built up in sample vessel 15 may escape through recess 655 and venting space 675. Cross-contamination of these escaping elements is significantly reduced because vertical edge 670 separates sample vessel 15 from an adjacent sample vessel 15. Moreover, gas flow from cannula 22 maintains a positive pressure within sample vessel 15 such that contaminants outside sample vessel 15 are not drawn in through venting space 675 into sample vessel 15 by way of recess 625. Other vents 610 may be configured such that excess gases, liquids, emulsions, or excess pressure may escape through vent 610 without cross-contaminating other sample vessels 15.

In another embodiment of gas distribution arrangement 270, illustrated in FIG. 2, array of sample vessels 110 is configured such that gas distribution arrangement 270 oxygenates, for example, each individual sample vessel 15 as opposed to utilizing a dispensing plate 645. Thus, array of sample vessels 110 may be oxygenated (or provided with other appropriate gas) collectively or individually by adjusting cannula assembly 80 for any individual sample vessel 15. For example, in one application, section A may be oxygenated (or provided with other appropriate gas) twice as long as section B.

In the illustrated example, array of cannula 120 corresponds to array of sample vessels 110, which is composed of individual sample vessels 15. Each individual sample vessel 15 also corresponds to an individual cannula assembly 80 which is connected to distributor 55. Oxygen and/or one or more other gases are delivered to distributor 55 through manifold connector 65. Oxygen and/or one or more other gases may be delivered through each cannula assembly 80, or selectively to certain assemblies 80. For example, cannula assemblies 80 in sections A and B may be utilized, while no gases flow to sections C and D.

Referring to FIGS. 3 and 12, gripping surface 17 allows for automated or manual transfer of sample vessel 15 to and from the fermentation apparatus or another processing station. In one embodiment, gripping surface 17 is magnetic such that a magnet attracts gripping surface 17 and transfers the sample vessel to another processing station. In another embodiment, a gripping mechanism grips the outer sides of the sample vessel to effect transfer. In yet another embodiment, gripping surface 17 is a lip at the top of the sample vessel. Other surfaces that may be gripped in order to transport the sample vessel to or from the fermentation processing station are within the scope of the present invention. For example, gripping surface 17 may be on the inside, outside, top or bottom of sample vessel 15.

In a particular embodiment, individual sample vessel 15 is constructed of Pyrex glass, but other suitable materials may be used to construct sample vessel 15. For example, plastic, ceramic, aluminum, or any other material may be used that is non-reactive to fermentation medium 20 or to other materials involved in additional processes contemplated in a multiple process production, such as in a high throughput system. It will further be appreciated that fermentation medium 20 may be the same medium in each individual sample vessel 15 or, alternatively, array of sample vessels 110 may include a combination of different fermentation mediums. For example, fermentation medium 20 may be the same in each individual sample vessel 15 and contain the same fermentation broth for a bulk synthetic process. Alternatively, each fermentation medium 20 in array 110 may have a slightly different fermentation broth in order to optimize the production yield of a certain component.

FIG. 12 illustrates a preferred embodiment of gas distribution arrangement 270 and cannula 22. In this example, oxygen, a mixture of oxygen and other gases, or another gas or gas mixture is introduced into dispensing plate 645 through inlet 630. Fasteners such as screws connect and align upper portion 647 to bottom portion 646 through apertures 640. Dispensing tube 760 and cannula 22 are directly attached to dispensing plate 645 and can be replaced by unfastening portions 646 and 647, replacing either or both dispensing tube 760 or cannula 22, and refastening portions 646 and 647. It is preferable for dispensing tube 760, cannula 22, inlet 630, and portions 646 and 647 to remain fastened together such that these elements are autoclaved as one unit. This allows for significant sterilization without the time and cost expense of dismantling arrangement 270 after each fermentation in order to separately sterilize each element.

In the illustrated example, a top surface of individual sample vessel 15 abuts directly onto surface 660 within sample vessel area 625. The top surface of sample vessel 15 is positioned within recess 655. Surface 660 preferably is not in contact with the entire circumference of the top surface of sample vessel 15. Also preferably, vent 610 is positioned adjacent to surface 660 such that a gap 672 exists between surface 660 and the vertical edge of sample vessel 15, thereby creating a passage for excess gases, emulsions, or pressure to escape from sample vessel 15 through venting space 675. Gas flow through cannula 22 provides sufficient pressure such that contaminants are not drawn into sample vessel 15 through venting space 675.

When fermentation is complete, transportable container frame 250 transports array of sample vessels 110 from water bath 240, or any other temperature controlled area 210, to the next processing station. For example, transportable container frame 250 may either manually or automatically transport array 110 to a centrifuge processing station. In one embodiment, the centrifuge processing station includes a centrifuge and a surface to hold container frame 250. Individual sample vessels, either collectively, in groups, or singly, may be transferred from the container frame to the centrifuge by manipulating gripping surface 17. Further processing steps may be conducted directly on the sample contained in each individual sample vessel 15 without transferring the sample out of sample vessel 15.

II. An Automated Fermentation Apparatus

Figure 7:
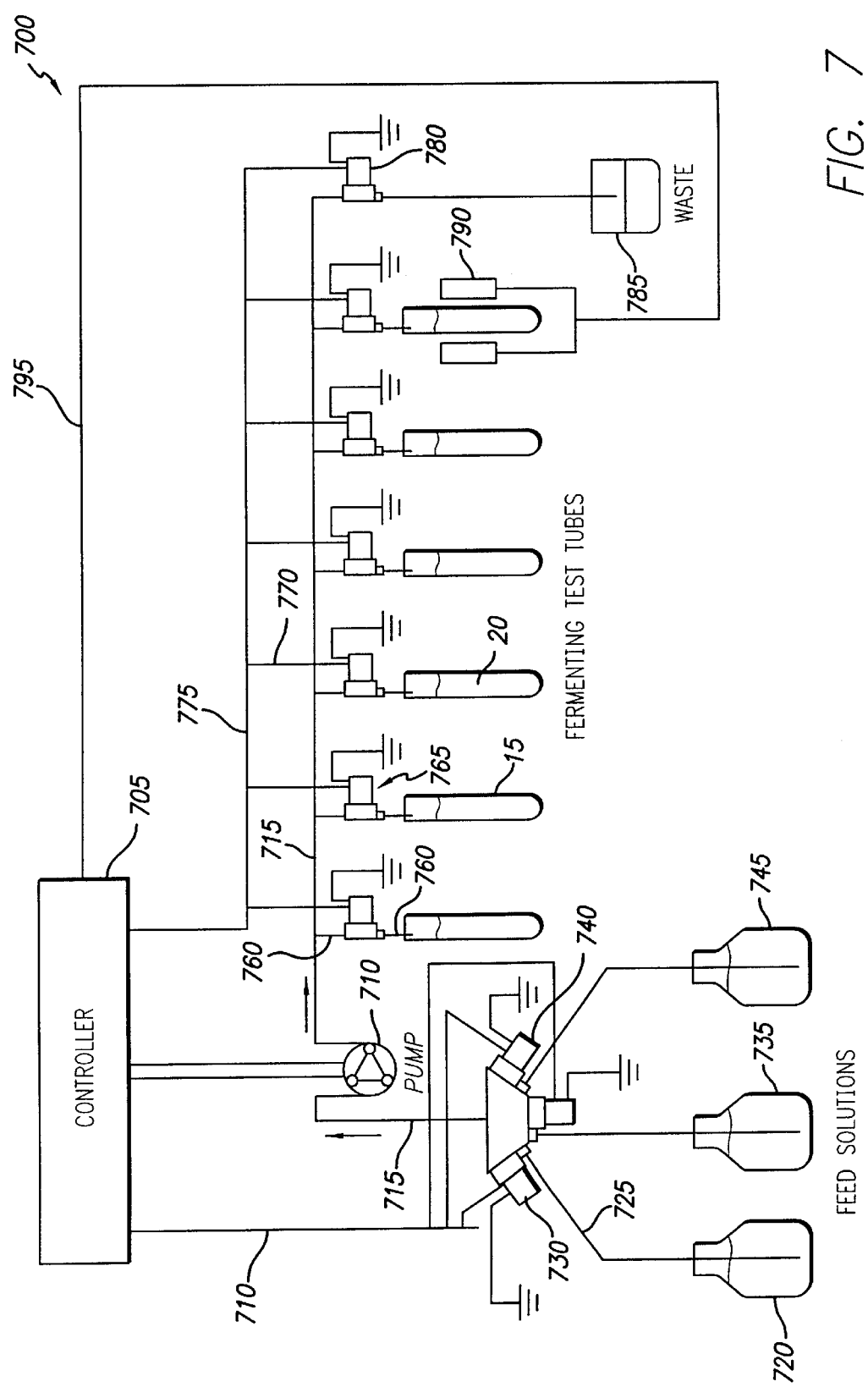
FIG. 7 is an automated fermentation assembly in accordance with the present invention.

FIG. 7 illustrates a preferred embodiment of an automated fermentation apparatus 700. A process controller 705 monitors and controls various components of apparatus 700 and preferably is a programmable computer with an operator interface. Alternatively, process controller 705 may be any suitable processor that coordinates multiple components of apparatus 700, such as timing mechanisms, adding solutions, adjusting temperature, adjusting gas flow rates and gas mixtures, detecting measurements, and/or sending an alarm or notification prompting operator intervention. Electronic couples 710, 755, and 795 connect various components of fermentation apparatus 700 to process controller 705. For example electronic couple 710 enables controller 705 to start, stop and monitor solution flow from feed solutions 720, 735, and 745. Likewise, electronic couple 775 enables controller 705 to start, stop and monitor reagent dispensing into sample vessels 15. Electronic couple 795 also enables controller 705 to transmit and receive information from sensors 790 as well as monitor and adjust temperature controlled areas 210. Other coupling devices may also be used in the present invention.

In one embodiment of fermentation apparatus 700, feed solutions 720, 735, and 745 are pumped (either singly, in combination, sequentially, or collectively) from individual feed tubes 725 into dispensing tube 715. Selecting the appropriate solenoid determines which feed solution is pumped through dispensing tube 715. For example, solenoid 730 controls flow from feed solution 720 through feed tube 725. In another application, a mixture of feed solutions 720 and 735 are simultaneously pumped into dispensing tube 715. In another application, feed solution 720 is fed into dispensing tube first, followed by an incubation period (directed by controller 705), followed by feed solution 735 being pumped into dispensing tube 715. Different combinations of feed solutions may be used and more or fewer feed solutions may be used with apparatus 700 according to any specific application.

Using a pump 710, such as a peristaltic pump, dispensing tube 715 transfers feed solution to an individual dispensing tube 760. Each individual dispensing tube 760 corresponds to an individual sample vessel 15 and tube 760 is positioned such that feed solution 720, for example, is transferred volumetrically from dispensing tube 760 into its corresponding sample vessel 15 once solenoid 765 is opened. Each solenoid 765 corresponds to an individual sample vessel 15. Volumetric dispensing of feed solutions is controlled by process controller 705 which preferably controls the amount, the rate and the time of dispensing. Dispensing tube 760 may be composed of plastic, metal, or any material that is non-reactive to the feed solution being dispensed.

In one embodiment, delivery solenoids 765 works in conjunction with a peristaltic pump 710 and controller 705 to deliver multiple feed solutions such as feed solutions 720, 735, and 745 into individual sample vessels 15. Each solenoid 765 corresponds to a sample vessel 15 and the solenoids 765 are manifolded together and fed by the output of a single peristaltic pump 710. Each solenoid 765 preferably opens sequentially in order to dispense a volumetric amount of feed solution 720. However, parallel addition is also contemplated within the present invention.

In one embodiment, feed solution 720 introduces nutrient into fermentation medium 20 through dispensing tube 715 using pump 710 and solenoid 765 to deliver solution 720 to individual dispensing tube 760. After addition of feed solution 720, solenoid 730 is closed and solenoid 740 corresponding to rinse solution 745 opens. Pump 710 delivers rinse solution 745 through dispensing tube 715, thereby rinsing dispensing tube 715 with solution 745, which is then flushed into waste container 785. Solenoid 780 controls flow from dispensing tube 715 into waste container 785. Feed solution 735 is then pumped through dispensing tube 715 and dispensed through tube 760. Dispensing tube 715 is rinsed again with rinse solution 745 before another addition. Solenoids 765 are preferably located very near to dispensing tube 760 in order to minimize dead volume downstream. In this way, dispensing tube 715 accurately delivers a known amount of feed solution 720 and 735 without cross contaminating or fouling the next or different addition of feed solution through dispensing tube 715. Accordingly, each addition is volumetrically precise with a minimal, known amount of feed solution from a previous addition diluting the next addition. In this way, feed solutions such as additional nutrients, trace minerals, vitamins, sugars, carbohydrates, nitrogen containing compounds, evaporating liquids, pH balancing compounds, buffers, and other liquids may be added to fermentation media 20 in an automated, yet highly precise manner.

Coordinated by process controller 705, various components may be activated either at pre-determined time intervals or in response to the measurement of some physical property within sample vessel 15. For example, in one embodiment, an operator programs process controller 705 to incubate sample vessels 15 for a pre-determined time period at a particular temperature, add a desired amount of feed solution 720, and incubate further for another pre-determined time period at a different temperature. Any suitable combination of fermentation conditions may be programmed into process controller 705.

In a preferred embodiment, process controller 705 coordinates temperature control, the addition of feed solutions, adjustment of gas rates and gas mixtures, incubation periods, and rinsing in response to data received from sensors 790. Sensors 790 may be located inside or outside of individual sample vessels 15. Sensors 790 can detect color changes spectrophotometrically, monitor evaporation rates, measure changes in optical density, detect light changes photometrically, detect pH changes, electrolytically measure redox potentials, monitor temperature fluctuations, or detect other physical changes and transmit this data to process controller 705. In response, process controller 705 accordingly adjusts various components of apparatus 700. For example, by measuring the redox potential, sensors 790 detect when a fermentation sample is being over-oxygenated or over-provided with another gas and process controller 705 accordingly adjusts the gas flow or gas mixture ratio. As another example, process controller 705 may respond to a change in pH, as detected by sensors 790, by adding a pH buffer from feed solution 720. In one embodiment, maximum protein expression may be detected by monitoring light emission, at which point fermentation is halted to minimize wasting fermentation resources after optimum fermentation yield has been reached.

Because of the uniformity of each fermentation medium 20, cannula 22, and dispensing of feed solutions 720, very few, for example, one sensor 790 is all that is necessary to monitor the entire array of sample vessels 110. Alternatively, when sample vessels 15 contain different fermentation media 20 or undergo different fermentation conditions, numerous sensors 790 may be employed.

III. Method Of Using A Multiple-Sample Fermentor

Figure 4:
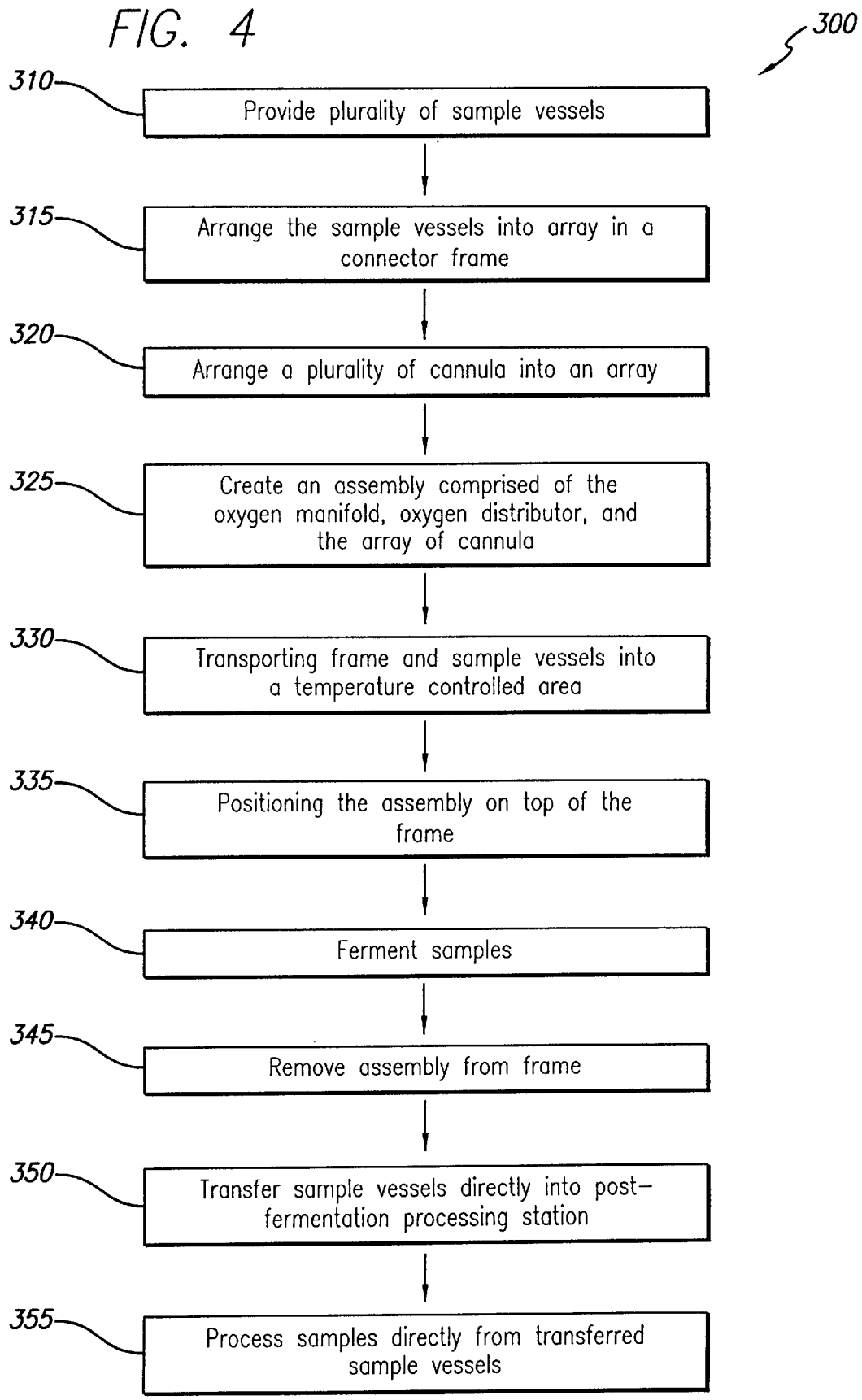
FIG. 4 is a block diagram of a fermentation method in accordance with the present invention.

FIG. 4 describes the fermentation method 300 practiced in accordance with the present invention. Block 310 provides for a plurality of sample vessels 15. By providing a number of smaller volume fermentation vessels, this method is more advantageous than production scale fermentation methods that use bulk fermentation vessels, in that smaller volumes of growth medium are more predictable in their yield and nutrient needs than are standard production scale volumes that are utilized in bulk fermentation methods. The number of sample vessels that may be fermented at any one time is unlimited by the present invention, and instead is only limited either by the configurational practicalities of any one fermentation apparatus or by the number of sample vessels that may be handled by further processing steps in the production.

Block 315 arranges sample vessels 15 into an array 110. Array 110 may be configured in any shape that is practicable for the fermentation apparatus. For example, sample vessels 15 may be arranged in a rectangular array, a honeycomb configuration, or a linear array.

Block 320 arranges a plurality of cannula 22 into an array 120. According to the present invention, each cannula 22 in this cannula array 120 corresponds to an individual sample vessel 15 in the sample vessel array 110 arranged in block 315. In one embodiment, the plurality of cannula is limited by the number of sample vessels 15 arranged in block 315.

Block 325 creates an gas distribution arrangement 270 for delivering oxygen and/or one or more other gases to fermentation media 20 in sample vessels 15. For example, one embodiment fastens cannula array 120 to gas distributor 55, which is connected to manifold 75. Cannula array 120 may be fastened by any means achieving a liquid-tight seal. For example, cannula 22 may be connected via a union connector to gas distributor 55. Alternatively, cannula 22 may be pneumatically connected to the distributor 55, or cannula 22 and gas distributor 55 may be molded as a single unit. In another embodiment, distributor 55 connects directly to an gas source 85 without using manifold 75. The method of creating gas distribution arrangement 270 may be achieved by any method of uniformly delivering oxygen and/or one or more other gases from a gas source 85 to a gas distributor 55 such that gas is delivered to each individual sample vessel 15 selectively or collectively by way of a corresponding cannula 22.

Block 330 transports container frame 250 containing sample vessels 15 to a temperature controlled area 210. Other methods used to control temperature know in the art are also contemplated within the present invention. For example, container frame 250 may be transported to a heated gel bath or a controlled temperature room used to maintain a constant temperature.

Block 335 positions gas distribution arrangement 270 created in block 330 on top of container frame 250. From this configuration, the array of sample vessels are fermented in block 340.

Once fermentation is complete, block 345 removes gas distribution arrangement 270 from container frame 250. Sample vessels 15 are transferred from container frame 250 directly to a post-fermentation processing station in block 350 by manipulating a gripping surface 17 located on each sample vessel. This post-fermentation processing station includes any processing step where the fermentation product may be processed directly from the sample vessel. For example, array of sample vessels 120 may be transferred, either manually or robotically, from the container frame directly to an automated centrifuge. Alternatively, sample vessels 15 may be transferred to an aspirating station or detecting station.

In block 350, the fermentation product in sample vessels 15 are directly transferred into a post-fermentation processing station and in block 355 the fermentation product is directly processed in the sample vessels themselves. For example, in one embodiment, sample vessels 15 are transferred directly to a centrifuge station in which sample vessels 15 are positioned directly inside the centrifuge such that sample vessels 15 act as centrifugation tubes and the fermentation product is centrifuged according to methods known in the art. Further processing steps such as aspirating reagent dispensing, or detecting may also occur directly in the sample vessel used in the fermentation process. In this way, the fermentation vessel provides a sample vessel that holds the sample throughout the entire production process, thereby eliminating excess waste from transferring sample material from sample vessel to sample vessel as well as decreasing the cost of washing and sterilizing a fermentation apparatus in addition to sample vessels from each production process step. Other multiple process productions or analyses may also be practiced in accordance with the present invention.

Figure 5:
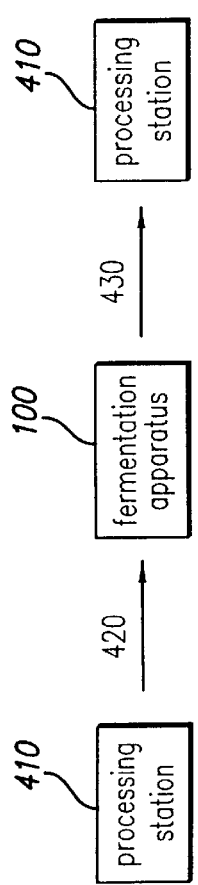
FIG. 5 is a block diagram showing the use of a fermentation system within a multiple process procedure in accordance with the present invention.

In FIG. 5, a block diagram 400 is shown wherein the present invention is integrated into a multiple step, multiple process production. Block 410 depicts a processing station prior to fermentation. In one embodiment, fermentation broth and fermentation nutrients are added to sample vessels 15 at prior processing station 410. Other processing steps involved in a multiple step production or analysis are also contemplated in accordance with the present invention. For example, bacteria colonization may occur in sample vessels 15 at a prior processing station 410. A transporter 420 transfers the sample vessel from processing station 410 to a fermentation apparatus such as fermentation apparatus 10. Other embodiments of a fermentation apparatus practiced in accordance with this invention may also be used. For example, fermentation apparatus 700 may also be used.

It will further be appreciated that transporter 420 may transfer the sample vessels individually, in groups, or in an array configured for the fermentation apparatus. For example, in one embodiment, container frame 250 transports the sample vessel array 110 to fermentation apparatus 10. Similarly, transporter 430 transports sample vessels 15 from a fermentation apparatus to a post-fermentation processing station 410. In one embodiment, transporter 430 transports container frame 250 holding array of sample vessels 110 to a centrifuge processing station 410. Post-processing station 410 may also be any other processing step occurring in a multiple process or analysis, such as an aspirating step, a dispensing step, or a detecting step. In this manner, multiple processing steps may be executed on a sample contained in the same sample vessel, thus enabling fermentation processes to be incorporated into high throughput or other multiple process systems.

One skilled in the art will appreciate that the present invention may be practiced by other than the preferred embodiments which are presented in this description for purposes of illustration and not of limitation, and the present invention is limited only by the claims which follow. It is noted that equivalents for the particular embodiments discussed in this description may practice the invention as well.

What is claimed is:

1. A fermentation apparatus comprising:
   (a) a container frame configured to contain a plurality of sample vessels; and,
   (b) a gas distribution arrangement that is configured to provide gas to the plurality of sample vessels when the sample vessels are positioned in the container frame, wherein the gas distribution arrangement comprises an array of cannulas, wherein one or more cannulas of the array of cannulas extends into a liquid in a sample vessel.

2. The fermentation apparatus of claim 1, wherein the gas distribution arrangement comprises a gas inlet configured to deliver gas to the array of cannulas, which cannulas are configured to provide gas to the sample vessels when the sample vessels are positioned in the container frame.

3. The fermentation apparatus of claim 1, wherein the gas distribution arrangement comprises:
   (1) a dispensing plate that comprises a top portion and a bottom portion, wherein the bottom portion and the top portion are joined together such that a hollow space exists between the top portion and the bottom portion;
   (2) an array of sample vessel areas located in a bottom surface of the bottom portion, which sample vessel areas each comprise a recess and are positioned to correspond to an array of sample vessels;
   (3) the array of cannulas that are in fluid communication with the hollow space and protrude from a bottom surface of the dispensing plate through the sample vessel areas; and,
   (4) a gas inlet in fluid communication with the hollow space for delivering gas into the plurality of sample vessels via the cannulas during fermentation.

4. The fermentation apparatus of claim 3, wherein each of the cannulas comprises a plurality of passages.

5. The fermentation apparatus of claim 4, wherein each of the cannulas comprises at least three passages.

6. The fermentation apparatus of claim 3, wherein the gas distribution arrangement is configured to allow delivery of one or more reagent to the sample vessels.

7. The fermentation apparatus of claim 1, wherein the container frame is configured to contain an array of sample vessels.

8. The fermentation apparatus of claim 7, wherein the container frame is configured to contain an 8 by 12 array of sample vessels.

9. The fermentation apparatus of claim 7, wherein the container frame is configured to contain at least 96 sample vessels.

10. The fermentation apparatus of claim 9, wherein the container frame is configured to contain 96, 384, or 1536 sample vessels.

11. The fermentation apparatus of claim 1, wherein the container frame is transportable.

12. The fermentation apparatus of claim 11, wherein the container frame is configured for transport to a post-fermentation processing station.

13. The fermentation apparatus of claim 1, wherein the container frame is configured for placement within a temperature controlled area, wherein a temperature controller is coupled to the container frame and/or to the plurality of sample vessels.

14. The fermentation apparatus of claim 13, wherein the temperature controlled area comprises a water bath or a temperature controlled room.

15. The fermentation apparatus of claim 1, wherein the gas distribution arrangement is autoclavable.

16. The fermentation apparatus of claim 1, further comprising the plurality of sample vessels.

17. The fermentation apparatus of claim 16, wherein each sample vessel comprises a sample.

18. The fermentation apparatus of claim 17, wherein the samples each have substantially the same composition.

19. The fermentation apparatus of claim 17, wherein the samples each have a different composition.

20. The fermentation apparatus of claim 16, wherein the sample vessels comprise glass, plastic, metal, and/or ceramic.

21. The fermentation apparatus of claim 16, wherein one or more of the sample vessels comprises a vent.

22. The fermentation apparatus of claim 16, further comprising a sensor in contact with one or more of the samples in the sample vessels.

23. The fermentation apparatus of claim 1, wherein the gas distribution arrangement comprises a gas source which gas source provides oxygen or a mixture of oxygen and at least one other gas to each sample vessel during operation of the apparatus.

24. The fermentation apparatus of claim 1, further comprising a process controller operably coupled to the gas distribution arrangement.

25. The fermentation apparatus of claim 1, further comprising a dispenser for dispensing one or more reagents into the plurality of sample vessels.

26. The fermentation apparatus of claim 25, wherein the dispenser is configured to dispense the reagents into the plurality of sample vessels via a plurality of apertures that correspond to the sample vessels.

27. The fermentation apparatus of claim 16, wherein the sample vessels are centrifuge tubes.

* * * * *